(12) United States Patent
Yamagata et al.

(10) Patent No.: US 7,650,804 B2
(45) Date of Patent: Jan. 26, 2010

(54) MECHANOCHEMICAL SENSOR

(75) Inventors: Yutaka Yamagata, Wako (JP); Kozo Inoue, Tokyo (JP); Hitoshi Ohmori, Wako (JP); Joon-wan Kim, Wako (JP)

(73) Assignees: Riken, Wako-shi (JP); Fuence Co., Ltd., Tokyo (JP)

( * ) Notice: Subject to any disclaimer, the term of this patent is extended or adjusted under 35 U.S.C. 154(b) by 0 days.

(21) Appl. No.: 10/566,355

(22) PCT Filed: Jul. 27, 2004

(86) PCT No.: PCT/JP2004/010657

§ 371 (c)(1),
(2), (4) Date: Jan. 30, 2006

(87) PCT Pub. No.: WO2005/012906

PCT Pub. Date: Feb. 10, 2005

(65) Prior Publication Data

US 2006/0219030 A1    Oct. 5, 2006

(30) Foreign Application Priority Data

Jul. 30, 2003    (JP) .............................. 2003-204075

(51) Int. Cl.
*G01L 1/22* (2006.01)
(52) U.S. Cl. ................................. 73/862.634
(58) Field of Classification Search ............ 73/862.634, 73/64.53
See application file for complete search history.

(56) References Cited

U.S. PATENT DOCUMENTS

| | | | | |
|---|---|---|---|---|
| 4,478,093 A | * | 10/1984 | Valadier ................. | 73/862.633 |
| 4,666,198 A | * | 5/1987 | Heiserman ................. | 294/86.4 |
| 4,896,098 A | * | 1/1990 | Haritonidis et al. ......... | 324/663 |
| 5,444,244 A | * | 8/1995 | Kirk et al. ................. | 250/306 |
| 5,726,480 A | * | 3/1998 | Pister ......................... | 257/415 |
| 6,033,913 A | | 3/2000 | Morozov et al. | |
| 6,221,653 B1 | | 4/2001 | Caren et al. | |
| 6,474,787 B1 | * | 11/2002 | Cruz-Uribe ................. | 347/54 |
| 6,935,165 B2 | * | 8/2005 | Bashir et al. ............... | 73/64.53 |
| 6,941,823 B1 | * | 9/2005 | Lai et al. ............... | 73/862.639 |
| 2001/0016322 A1 | | 8/2001 | Caren et al. | |

(Continued)

FOREIGN PATENT DOCUMENTS

JP    A-2002-243734    8/2002

(Continued)

OTHER PUBLICATIONS

J. Fritz et al.; "Translating Biomolecular Recognition into Nanomechanics"; *Science*; vol. 288; Apr. 14, 2000; pp. 316-318.

(Continued)

*Primary Examiner*—Lisa M Caputo
*Assistant Examiner*—Octavia Davis
(74) *Attorney, Agent, or Firm*—Oliff & Berridge, PLC

(57) ABSTRACT

There is provided a mechanochemical sensor including a minute mechanical structure body having the functional membrane formed at least on one part of its surface, a supporting part for supporting the minute mechanical structure body; and a detection part for detecting the change of a mechanical property of the minute mechanical structure body. According to the invention, it is possible to provide improved adhesion between the functional membrane and the minute mechanical structure body since the functional membrane is integrally formed in advance on the minute mechanical structure body, which will contribute to the increase of detection signal, and improvement of measurement precision and sensitivity.

15 Claims, 7 Drawing Sheets

U.S. PATENT DOCUMENTS

2005/0242479 A1* 11/2005 Petisce et al. ............... 264/650

FOREIGN PATENT DOCUMENTS

| JP | A-2003-136005 | 5/2003 |
| JP | A-2003-185665 | 7/2003 |
| WO | WO 98/50773 A2 | 11/1998 |
| WO | WO 01/33226 A1 | 5/2001 |

OTHER PUBLICATIONS

Morozov et al.; "Mechanical Detection of Interaction of Small Specific Ligands with Proteins and DNA in Cross-Linked Samples"; *Analytical Biochemistry*; vol. 201; pp. 68-79; 1992.

Yamagata et al.; "A new biosensor using mechano-chemical effect of micro protein film"; The Seventh World Congress on Biosensors 2002, Abstract Book A1.07; 2002.

Wu et al; "Bioassay of prostate-specific antigen (PSA) using microcantilevers"; Nature Biotechnology; vol. 19; Sep. 2001; pp. 856-860; XP002981300.

McKendry et al.; Multiple label-free biodetection and quantitative DNA-binding assays on a nanomechanical cantilever array; PNAS; vol. 99; No. 15; Jul. 23, 2002; pp. 9783-9788; XP002377192.

Lang et al; "An artificial nose based on a micromechanical cantilever array"; Analytica Chimica Acta; Elsevier; vol. 393; No. 1-3; 1999; pp. 59-65; XP000990018.

* cited by examiner

MECHANOCHEMICAL SENSOR

TECHNICAL FIELD

The present invention relates to a mechanochemical sensor. In particular, the present invention relates to a mechanochemical sensor for detecting chemical reaction occurring in a functional membrane by detecting the mechanical deformation of the functional membrane.

RELATED ART STATEMENTS

Some materials have been found to alter their mechanical properties depending on the content of minute amounts of various substances therein, and such a material has been used as a means for detecting minor or trace components contained in a sample. However, according to the conventional technique, a membrane material is prepared separately that serves as a detector having a detection function, and the material is mounted to a mechanical property measuring apparatus for measurement. Therefore, it has been impossible to miniaturize the material having a detector function sufficiently, and thus the resulting detector has been problematic in its detection speed and sensitivity. In addition, when the membrane material is attached to or detached from a measuring apparatus, stresses and strains may develop in the material, or adhesion of the material to the receiving member of apparatus may decline during measurement. These factors often cause errors in measurement.

Take, as an example of the conventional mechanochemical detection method, the one introduced by Morozov and others for detecting interaction between a ligand and a polymer material (see Victor Morozov, et al., "Detection of ligand interaction with polymeric material," U.S. Pat. No. 6,033,913, Victor Morozov and Tamara Morozova (Inventors), and New York University (Assignee); Victor N. Morozov and Tamara Ya. Morozova, "Mechanical detection of interaction of small specific ligands with proteins and DNA in crosslinked samples," Analytical Biochemistry 201, pp. 68-79 (1992)). The method by Morozov et al. also suffers from the same problems as described above.

Another conventional technique based on pick-up detection has been introduced by Yamagata and others (see Y. Yamagata, V. N. Morozov, K. Inoue, J. Kim, H. Ohmori, T. Higuchi, "A new biosensor using mechano-chemical effect of micro protein film," The Seventh World Congress on Biosensors 2002, Abstract Book, A1.07 (2002)). According to this method, it is necessary for picking up chemical reaction to penetrate a fine probe through a sample such as a functional polymer or a protein in the form of a membrane or thin layer, and this operation itself requires very difficult manipulation. In addition, even when the probe is successfully passed through a sample, concentrated stress will develop around the hole formed as a result of probe penetration that will interfere with the precise detection of the change of a physical property of the sample such as a functional polymer or a protein (i.e., such stresses if present will reduce signal). This method further requires a considerable volume of a solution containing minute amounts of substances or minor components as a medium used for detection of a sample. Moreover, if it is required to perform measurement on two or more functional materials, replacement of one material with another for each renewed measurement requires considerable handling and time, and error due to the variation, for example, in the placement position of functional materials will degrade the reproducibility of measurement. Furthermore, even if it is required to perform measurement on multiple functional materials, it is hardly possible to make parallel measurement on those multiple functional materials simultaneously.

For detecting the minute change of a mechanical property of a sample, a force sensor has been used, and the sensor must have a certain sizable size due to requirement imposed by its structure: if the size is lowered below the lower limit required by the structure, its detection sensitivity will be reduced below the desired level. A biosensor having a minute structure has been reported in a study using a self-assemble monolayer (SAM) (see J. Fritz, M. K. Baller, H. P. Lang, H. Rothuizen, P. Vettiger, E. Meyer, H. J. Guntherodt, C h. Gerber, J. K. Gimzewski, "Translating biomolecular recognition into nanomechanics," Science, vol. 288, pp. 316-318, April (2000)). However, since the sensor is based on a monolayer membrane, the detection signal is so small that a practical sensitivity cannot be obtained.

OBJECT OF THE INVENTION

The object of the present invention is to provide a mechano-chemical sensor capable of solving the problems described above in relation to conventional mechanochemical sensors.

SUMMARY OF THE INVENTION

A mechanochemical sensor according to the present invention comprises:
- a minute mechanical structure body having a functional membrane (i.e., thin sheet, film or thin layer) formed at least on one part of its surface;
- a supporting means for supporting the minute mechanical structure body; and
- a detection means (force sensor, optical deflection detector, non-contact deflection detector, etc.) for detecting the change of a mechanical property (at least one selected from physical properties including extension/contraction, strain, elastic coefficient, stress, etc.) of the minute mechanical structure body.

According to this aspect of the present invention, it is possible to detect chemical reaction occurring in a functional membrane by detecting the mechanical deformation of the membrane. According to this aspect of the invention, it is possible to provide improved adhesion between the functional membrane and the minute structure body since the functional membrane is integrally formed in advance on the minute mechanical structure body, which will contribute to the increase of detection signal, and improvement of measurement precision and sensitivity. In other words, according to the present invention, it is possible to mount a detector body incorporating a functional membrane for detecting the minute change of a physical quantity ready to act as a sensor to a sensor body, in contrast with a conventional sensor requiring the two-step operation involving the formation of a membrane, and detachment and attachment of membrane to and from a sensor body, and thus the technique of the present invention can eliminate the disturbing effects due to stresses developed in the interior of the membrane which would otherwise result from the detachment/attachment of membrane to and from a sensor body as are observed in a membrane prepared according to the conventional method, which allows precise measurement to be performed at a high sensitivity.

According to an embodiment of the mechanochemical sensor of the invention, the minute structure body comprises a first region having the functional membrane formed on its surface and a second region supported by the supporting means, the first region and the second region being separated from each other and the first region being a thin layer, membrane or sheet.

According to this embodiment of the present invention, it is possible to precisely detect the change of a mechanical property of a functional membrane at a high sensitivity by providing a membrane or layer as thin as possible in the first region. Moreover, since the first region is separated from the second region according to the invention, it is possible to prevent the second region from affecting the functional membrane present in the first region which further contributes to the improved precision and sensitivity of measurement. More specifically, since the structure body is supported at the second region which is separated from the region where the functional membrane is formed, the supporting itself could have hardly any effect on the physical property of the functional membrane formed on a surface of the structure body, which still further contributes to the improved precision and sensitivity of measurement.

According to another embodiment of the invention, the minute structure body is a plurality of minute structure bodies each comprising a different functional membrane, that is, the mechanochemical sensor preferably has a plurality of minute structure bodies each comprising a different functional membrane. For the sensor, it is possible by incorporating different functional membranes to detect one or more unknown substances in a test solution or to determine their respective contents in the solution at a single operation.

According to yet another embodiment of the invention, the mechanochemical sensor preferably comprises the functional membrane made of a biopolymer (for example, protein, etc.), or a synthetic polymer (for example, functional resin, synthetic fiber, synthetic rubber, etc.). However, other substances (for example, metals, inorganic substances) than those mentioned above may be used as well, as long as they can be formed into a thin membrane at the membrane formation region of minute structure body, and the membrane is adhered thereto with a sufficiently strong binding force, and can have certain interaction with a target substance.

According to yet another embodiment of the mechanochemical sensor of the invention, the functional membrane is formed directly on a surface of the minute structure body by electro-spray deposition (ESD).

According to this embodiment of the present invention, the ESD technique does not require the heating of a membrane material and thus it is possible to form a membrane at any desired temperature. Namely, ESD does not affect in any way the physical and biological activities of a functional material (e.g., protein) constituting a membrane, which will further contribute to the improved precision and sensitivity of measurement.

According to yet another embodiment of the mechanochemical sensor of the invention, the functional membrane is formed directly on a surface of the minute structure body by ink jet deposition.

The Ink jet deposition technique provides many advantages: the apparatus required for the method is cheap and membrane formation is highly reproducible. Both ink jet deposition and ESD allow very thin membranes to be formed at a high reproducibility.

According to yet another embodiment of the mechanochemical sensor of the invention, the detection means has a zone or portion (zone acting as the fulcrum of a "lever," for example, like hinge and the like) which will not be displaced or displaced negligibly even when a mechanical property of the functional membrane is changed, and the minute structure body has its one end immersed into a test solution such that said zone is close to the surface of the test solution.

According to this embodiment of the invention, when this stationary zone or low displacing zone is put close to the surface of a test solution, it is possible to eliminate or reduce the disturbing effects from disturbances such as the surface tension of solution and fluctuation or ripples of the liquid surface, which will contribute to the improved precision of measurement.

According to yet another embodiment of the mechanochemical sensor of the invention, the detection means comprises a force-detection sensor and an actuator for providing a tension such as an initial tension to the functional membrane as described above.

According to this embodiment of the mechanochemical sensor of the invention, the minute mechanical structure body comprises a cantilever or one-end supported beam having the functional membrane formed thereon, and the detection means is a sensor (optical lever sensor, laser interferometer, etc.) capable of detecting the bending deformation of the cantilever of minute mechanical structure body.

By way of easily explanation the aspect of the present invention has been described as sensors i.e. devices, however it is understood that the scope of the present invention comprises methods substantially corresponding to the sensors.

For example, a method of the invention based on mechanochemical detection comprises the steps of:
  forming a functional membrane at least on one part of the surface of a minute mechanical structure body;
  supporting the minute mechanical structure body; and
  detecting the change of a mechanical property (at least one of the physical properties comprising extension/contraction, strain, elasticity coefficient, stress, etc.) occurring in the minute mechanical structure body using a sensor.

DETAILED DESCRIPTION OF THE PREFERRED EMBODIMENTS

First, detailed description of the principle of the present invention and its operation will be given.

According to the present invention, a functional material is applied to a minute structure body prepared in advance to be integrated thereto. This brings about many advantages: the functional material becomes small in size or miniaturized; handling of the functional material becomes easy; detection speed/sensitivity is improved; the medium for receiving a test sample is allowed to have a small volume; and the simultaneous detection of signals from plural samples is made possible. Since a minute structure body is very small in size, even if a material having a low compliance is used to constitute an elastic deformation-sensitive portion of the structure body, the portion can work satisfactorily because of size-effect, while it is still possible to maintain the resonant frequency of the portion at a high level. This allows the sensor to precisely detect the change of a mechanical property occurring in the functional membrane at a high sensitivity.

Direct formation of a functional membrane on a minute structure body makes it possible to greatly improve the binding intensity of the joint between the membrane and the structure body, which contributes to the enhancement of detection signals. According to the present invention, direct formation of a functional membrane on a minute structure body is achieved by electro-spray deposition or ink jet deposition. According to these methods, the resulting membrane has a larger thickness (100 nm to a few micrometers) than that of a mono-molecular layer, which also contributes to the enhancement of signals.

The embodiments of the present invention will be described in detail below with reference to the attached drawings.

Figure 1:
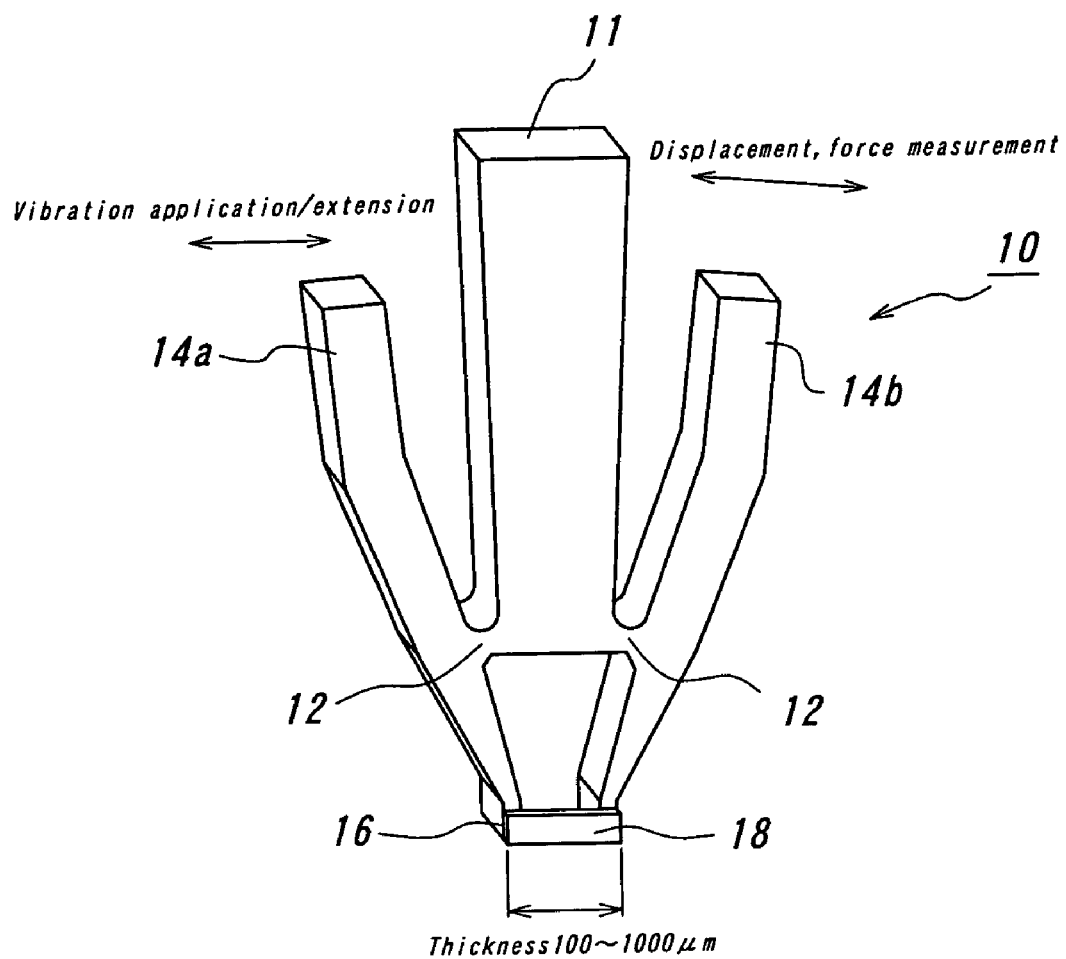
FIG. 1 is a diagram for showing the structure of an integrated type minute structure body (detector body) to be incorporated in a mechanochemical sensor of the invention.
Figure 1:
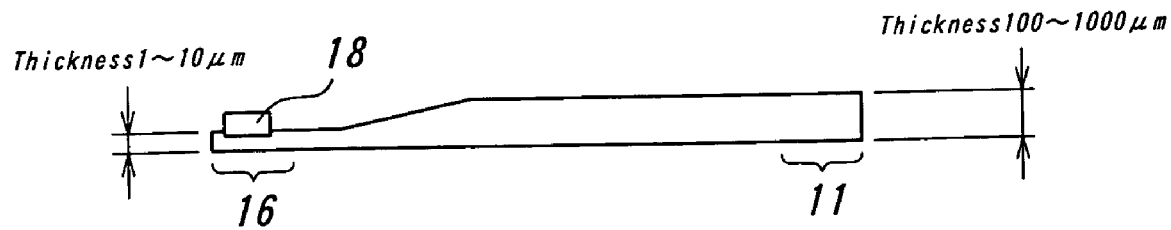

FIG. 1 is a diagram for showing the structure of an integrated type minute structure body (detector body) to be incorporated in a mechanochemical sensor of the invention. As shown in a diagram (perspective view) drawn in the upper portion of the figure, a detector body (integrated type minute structure body) 10 comprises a supporting portion 11 to serve as a joining portion to a sensor body, and a pair of arms 14a, 14b connected via elastic hinges 12 to supporting portion 11. One arm 14a of the pair of arms is connected to an actuator, while the other arm 14b is connected to a micro-force sensor. The lowest ends of the pair of arms form a thin space or region 16 for membrane formation as shown in a diagram drawn in the lower portion of the figure (lateral view). The space has, at the tip, a narrowed thickness of 1 to 10 μm (its lengthwise distance being about 100 to 1000 μm). Over the narrowed space is attached a functional polymer/protein chip or a functional membrane 18. Binding of the chip to the detector body may occur as direct adhesion via electro-spray deposition. Alternatively, a fixing agent such as carboxymethyl dextran may be coated in advance to the membrane formation area 16. Each elastic hinge portion 12 has a small width (about 1 to 10 μm) as compared with its thickness. The hinge portion 12 has a low rigidity to a force acting in a direction in parallel with the surface of the detector body viewed from front, while it has a high rigidity to a force acting in a direction normal to the above direction. Thus, when a protein membrane is stretched between the two arm ends, it is possible for the membrane to be moved only in its lengthwise (extension/ contraction) direction with the two arms acting as levers with their respective hinge portions as a fulcrum. This arrangement can minimize disturbing effects due, for example, to the twisting of the membrane which might otherwise occur. The lowest ends of both arms 14 are continuous to the two ends (force-acting points) of membrane formation area 16. Thus, for each of the pair of arms, its lowest end serves as a force-acting point, arm body 14 as a lever, and elastic hinge 12 as a fulcrum. The upper end of each arm 14 contacts with a sensor (not illustrated) or an actuator (not illustrated), i.e., the upper end of each arm 14 serves as an operation point of the above lever system. Thus, the detector body is so constructed as to allow the change of a mechanical property occurring in a functional membrane 18 applied to membrane formation area 16 to be measured at a high sensitivity.

Figure 2:
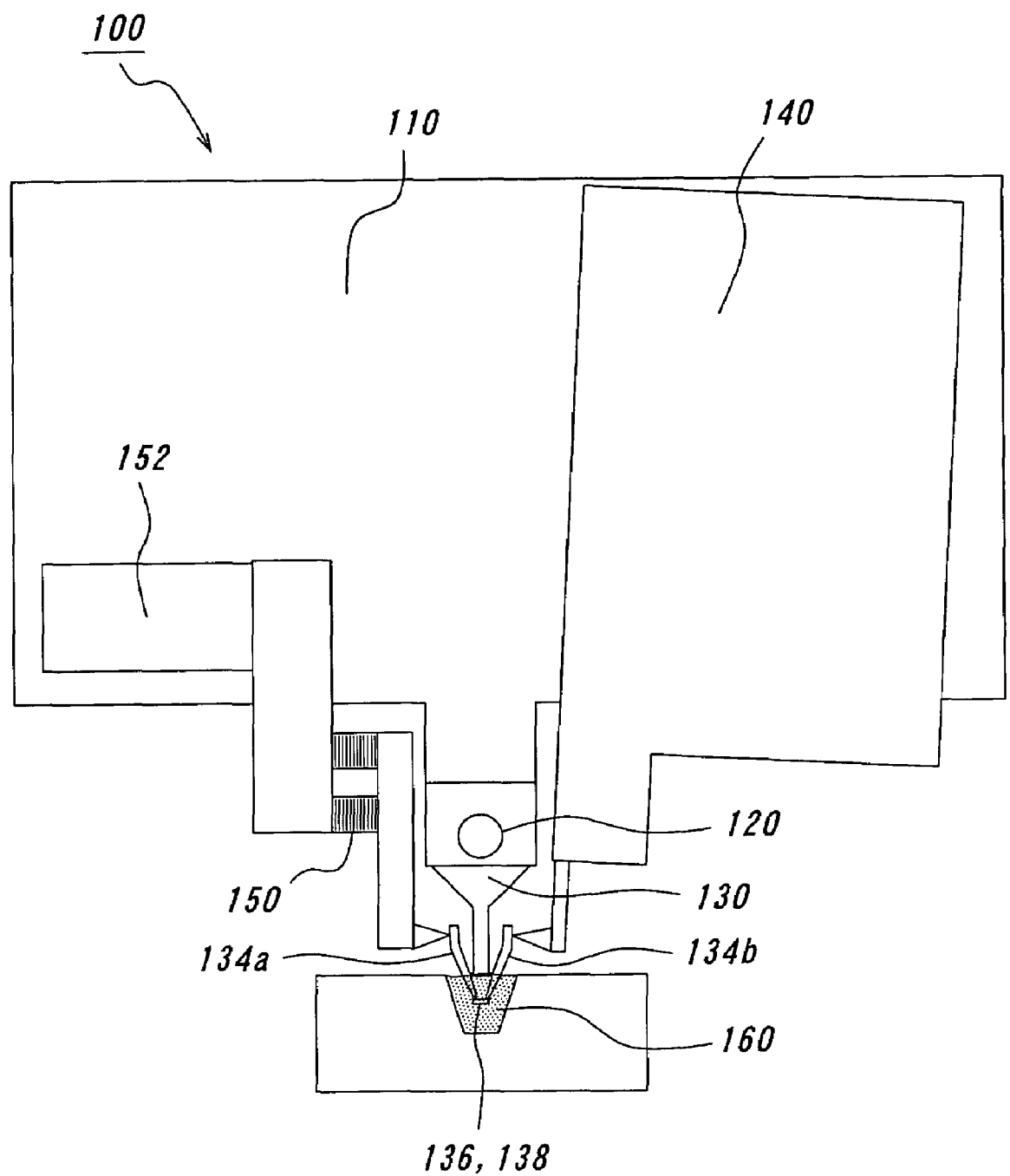
FIG. 2 is a diagram for illustrating the basic composition of a mechanochemical sensor of the invention incorporating the integrated type detector shown in FIG. 1.

FIG. 2 is a diagram for showing the basic composition of a mechanochemical sensor of the invention incorporating the integrated type detector shown in FIG. 1.

As shown in the figure, a mechanochemical sensor 100 comprises a base 110, a detector mount portion (supporting means) 120, an integrated type detector (detector body) 130, a micro-force sensor 140, a piezoelectric actuator 150, a finely adjustable stage 152, and a flow cell 160. The integrated type detector 130 is supported by the detector mount portion 120 attached to base 110. The integrated type detector 130 comprises an arm 134a kept in contact with the piezo-electric actuator 150, another arm 134b kept in contact with the micro-force sensor 140, a membrane formation area 136, and a functional membrane 138 (which is made of a protein in this particular embodiment) formed on the membrane formation area. The sensor also includes an A/D converter for converting detection signals into corresponding digital signals, a DSP, a display for presenting detection results in graphs, a memory device for storing measurement results, and a controller for controlling the actuator, stage and micro-force sensor, although they are not illustrated here.

The mount portion for holding the integrated type detector 130 has a comparatively wide area (the diameter being about 1 to 5 mm), and is sufficiently strong to withstand the handling by the user. Therefore, the user can easily handle the mount portion, for example, by holding it with a forceps. The piezoelectric actuator 150 is an element capable of effecting a displacement of 1 to 150 μm, and is used for applying an extension/contraction vibration to a protein membrane, which is in turn used for determining the elastic coefficient of the membrane. The force sensor 140 has a resolution of 1 μN or lower, and detects a force developed as a result of the extension/contraction of the protein membrane via the right-hand arm (lever), thereby determining the extension/contraction of membrane or the change of its elastic coefficient produced by the interaction between a functional polymer/ protein constituting the membrane and a target substance.

Figure 3:
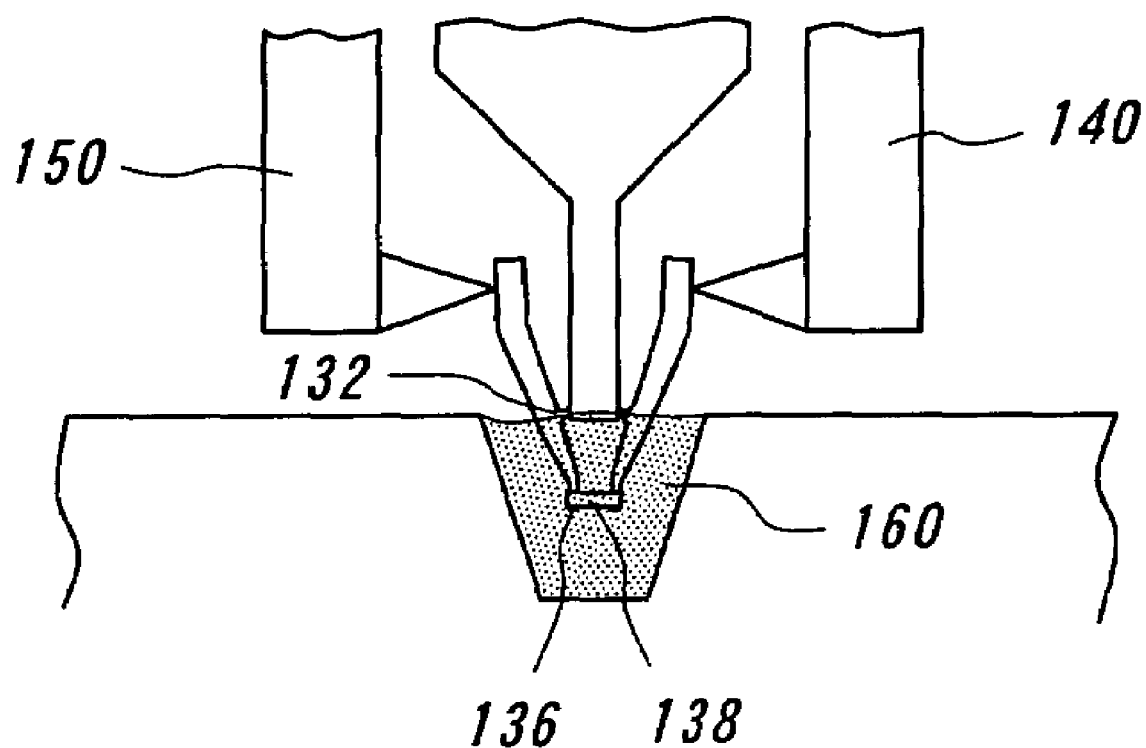
FIG. 3 is a diagram for depicting the detailed composition of a flow-cell portion (for reducing surface ripples) of the integrated type detector.

FIG. 3 is a diagram for showing the detailed composition of a flow-cell portion (for reducing surface ripples or fluctuations) of the integrated type detector.

The membrane formation area 136 and functional membrane (protein chip) 138 provided at the tip portion of detector are dipped in a flow-cell 160 where a solution containing a target substance is allowed to flow. Usually, through the flow-cell 160 are flowed a buffer for keeping the pH at a constant level and a solution containing a target substance alternately to check whether the presence of the target substance causes reaction to develop. During this operation pumps work for driving or evacuating solutions to or from the flow-cell and resulting pulsations and vibrations cause ripples to develop on the surface of solution in the flow-cell 60. Both the flow-cell 160 and the protein chip have such a tiny size that the surface tension of solution has a great effect on the chip in terms of a force per unit area, and thus, unless otherwise treated, ripples could act as an external factor interfering with the detection of signals. However, according to the arrangement of the detector with respect to the flow-cell shown in the figure, the hinge portions are placed close to the surface of solution in the flow-cell so as to minimize the effect of surface tension or ripples/fluctuations on the detector. This is because the displacement of lever (arm) close to the hinge portion 132 is infinitesimal (because each hinge 132 acts as a fulcrum of the lever), and thus even if the hinge portion is exposed to an external force, the force has a negligible effect on the detector. Generally, if a sensor detects the mechanical deformation in elasticity of an element of a minute structure body immersed in fluid, it is possible to greatly suppress external disturbing effects, for example, due to surface tension by placing the most displacement-free portion of the structure body close to the surface of fluid. The flow-cell is connected to a fluid supply apparatus (pump or the like) capable of supplying fluid at a constant rate, although the apparatus is not illustrated here. Since the mechanical property is very sensitive to the surrounding temperature, the entire sensor body (or at least the part of detector body comprising a functional membrane and arm portions) is preferably equipped with a thermostat apparatus or a thermo-control apparatus (not illustrated) so that the sensor body can be kept at a desired constant temperature.

In order to enhance the sensitivity of the sensor, it is also possible to introduce a displacement enhancing/extending device into the minute structure body. Furthermore, when plural minute structure bodies (incorporating respective different functional membranes made of different materials) are employed, it is possible to prepare the same number of flow-cells to be assigned to those different structure bodies so that different test solutions containing different solutes can be brought into contact with desired respective membranes.

Figure 4:
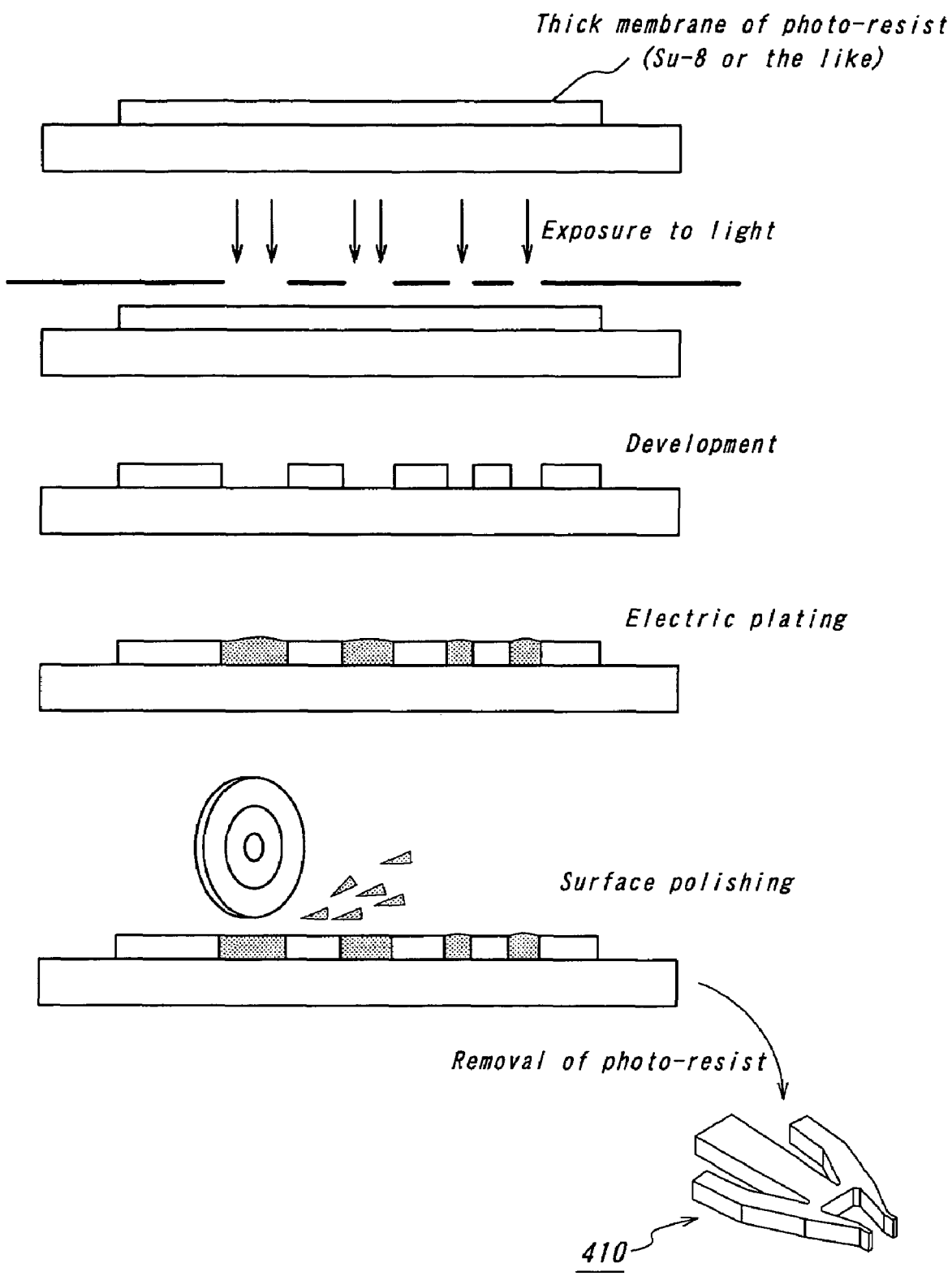
FIG. 4 is a flowchart for showing the steps (photolithography+fine mechanical processing) necessary for the manufacture of a minute structure body which will serve as a detector body.

FIG. 4 is a flowchart for showing the steps (photolithography+fine mechanical processing) necessary for the manufacture of a minute structure body which will serve as a detector body.

As shown in the figure, at first a thick coat is formed on a wafer by applying photo-resist (SU-8) thereto, and the wafer assembly is exposed to light via a mask, and subjected to development. As a consequence, a photo-resist negative image of a minute structure body is formed. This process may be replaced by another process based on the use of X-ray. Metal such as nickel, chromium or the like is deposited on the wafer assembly carrying the photo-resist negative image of a structure body so that the metal deposition represents the structure body. The resulting metal structure body, however, has a surface whose flatness is seriously degraded, a phenomenon often observed with metal deposition. The degraded surface flatness is dealt with by ultra-fine polishing process (such as electrolyte in-process dressing (ELID)) so as to produce uniformly flat surface, or step surface if necessary. Then, the photo-resist is removed to produce a completed form of minute structure body 410. Thus, it is possible by the procedure described above to mass-produce minute structure bodies at low cost. Alternatively, it is also possible to produce minute structure bodies by machining such as ultra-fine machining, electric discharge machining or stamping.

Figure 5:
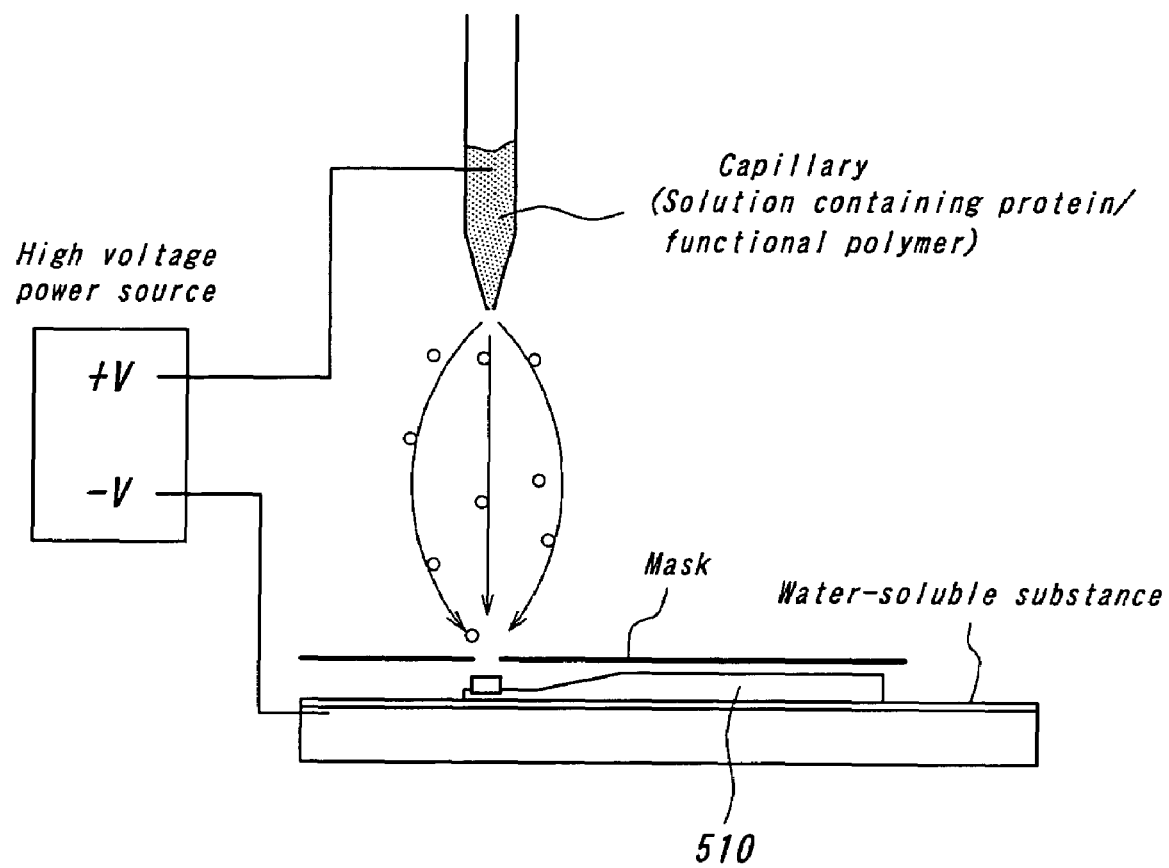
FIG. 5 is a schematic diagram for presenting an ESD-based method for forming a functional membrane on a detector body to be used according to the invention.

FIG. 5 is a schematic diagram for showing an ESD-based method for forming a functional membrane on a detector body to be used according to the invention. The procedure for forming a functional membrane (thin layer or film) on a minute structure body may be based on electro-spray deposition (ESD). A water-soluble polymer (e.g., PVP or the like) is applied or coated to a surface of a base underlying a minute structure body 510, and a membrane of a functional polymeric protein is formed above the polymer coat by ESD. Then, immobilization of the functional polymer is achieved by exposing the polymer to the vapor of a bridging agent (e.g., glutaraldehyde or the like). The assembly is then immersed in water to allow the underlying polymer to be removed by dissolution to water, thereby producing an independent minute structure body integrally incorporating a functional membrane. Even when a minute structure body incorporating a cantilever is used, it is possible to form a functional membrane by the same method as above without requiring the formation of a water-solution polymer coating.

It is also possible to form a membrane, in addition to electro-spray deposition, by other methods such as ink jet deposition, micro-stamping, vapor deposition using a piezo-electric actuator, vapor capture based on electrostatic attraction, spotting, etc.

It is possible to avoid the concentration of stresses at joints where a functional membrane is bound to a minute structure body by forming in advance a membrane of poly-L-lysine or the like which ensures a high mechanical strength at or around the joints which will contribute to the reinforcement of the functional membrane. Introduction of such reinforcement will enhance detection signals, thereby improving measurement sensitivity/precision, and further facilitate handling of the minute structure body.

Various methods are available for detecting the deformation of a minute structure body, that is, the change of a mechanical property of a functional membrane including the change of tension. The appropriate method may include, for example, methods using a cantilever, laser interferometer, electrostatic capacitance-based deflector, or optical deflector. Other methods than those described above that employ a sensor capable of detecting the elastic deformation of a part of a minute structure body may be used according to the invention. The sensor may be based on the use of a piezoresistive material or piezoelectric material, or an electrostatic capacitor.

A plurality of minute structure bodies incorporating respective functional membranes may be arranged in an array. Such an arrangement will be able to produce various systems having different functional implications: one system is for detecting an unknown trace or minor substance by using appropriately chosen different functional membranes; another system is for detecting multiple target substances simultaneously; and a yet another system where each minute structure body contains a flow-cell connected to micro-channels equipped with controlled valves is easy for handling and suitable for preventing signals from being affected by external disturbing factors.

Figure 6:
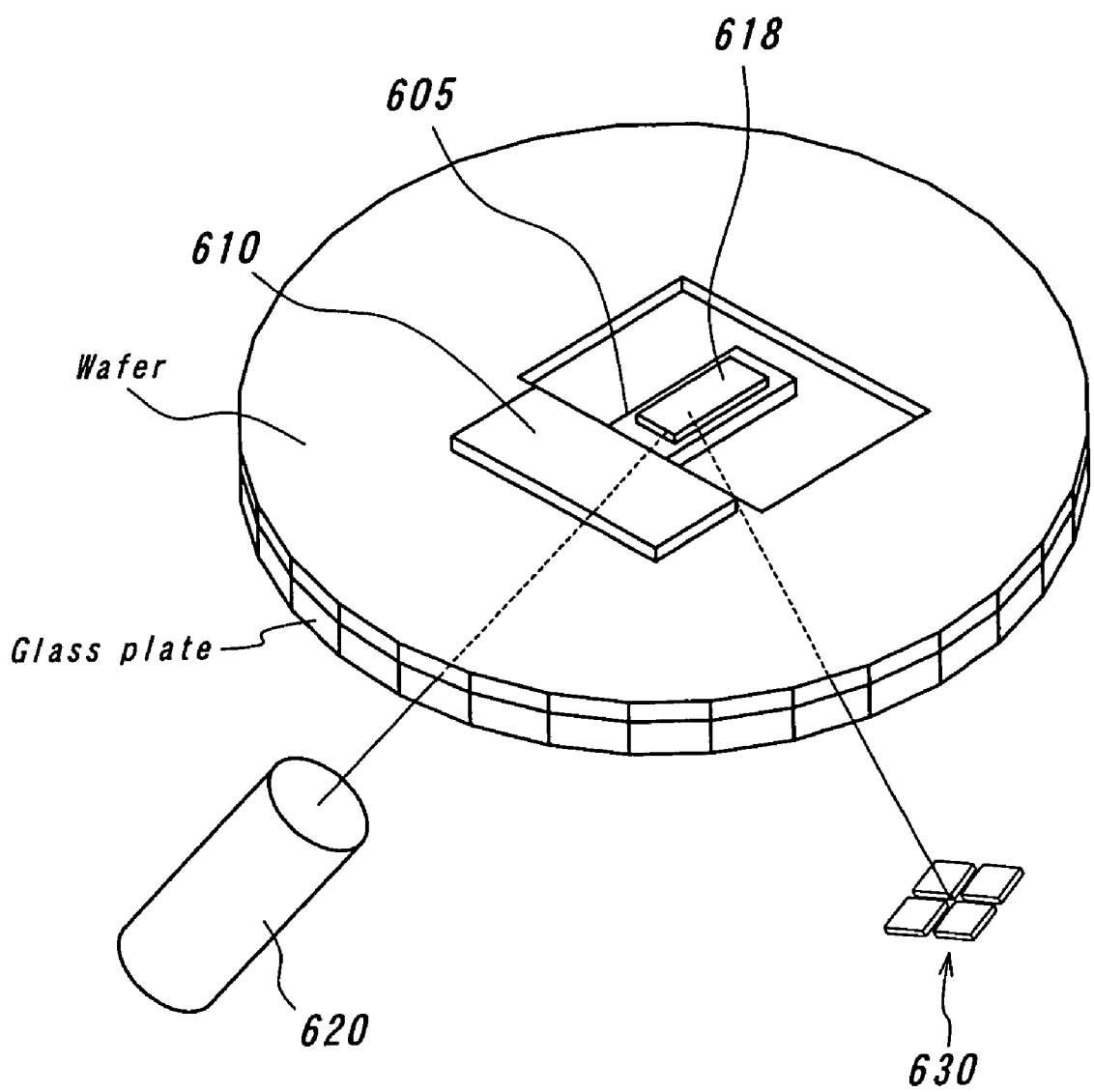
FIG. 6 is a diagram for showing the operation of a mechano-chemical sensor incorporating a minute structure body where a functional membrane is formed on the surface of a cantilever (one-end supported beam).

FIG. 6 is a diagram for showing the operation of a mechanochemical sensor incorporating a minute structure body where a functional membrane is formed on the surface of a cantilever (one-end supported beam).

As shown in the figure, a functional membrane 618 is formed or coated on the surface of the lever portion of a cantilever 610 which serves as a minute structure body. The functional membrane 618 is not independent, but is firmly attached to the surface of the cantilever. In this embodiment, when the change of a physical property (extension/contraction, or change of elasticity coefficient) of functional membrane 618 occurs, a change of tension arises at the surface of lever portion 605 which results in a change in bending amount of the lever portion. Detection of this change is achieved by allowing a laser source to emit a laser beam to the functional membrane 618 and a quadrant-cell photodiode 630 to receive reflected beam. For example, this change is detected by a cantilever, piezoresistive detector, or laser interference meter. The minute cantilever may be made of silicon, metals or plastics. Formation of a functional membrane on the surface of a cantilever may be achieved by ESD, ink jet deposition, screen printing, etc.

Figure 7:
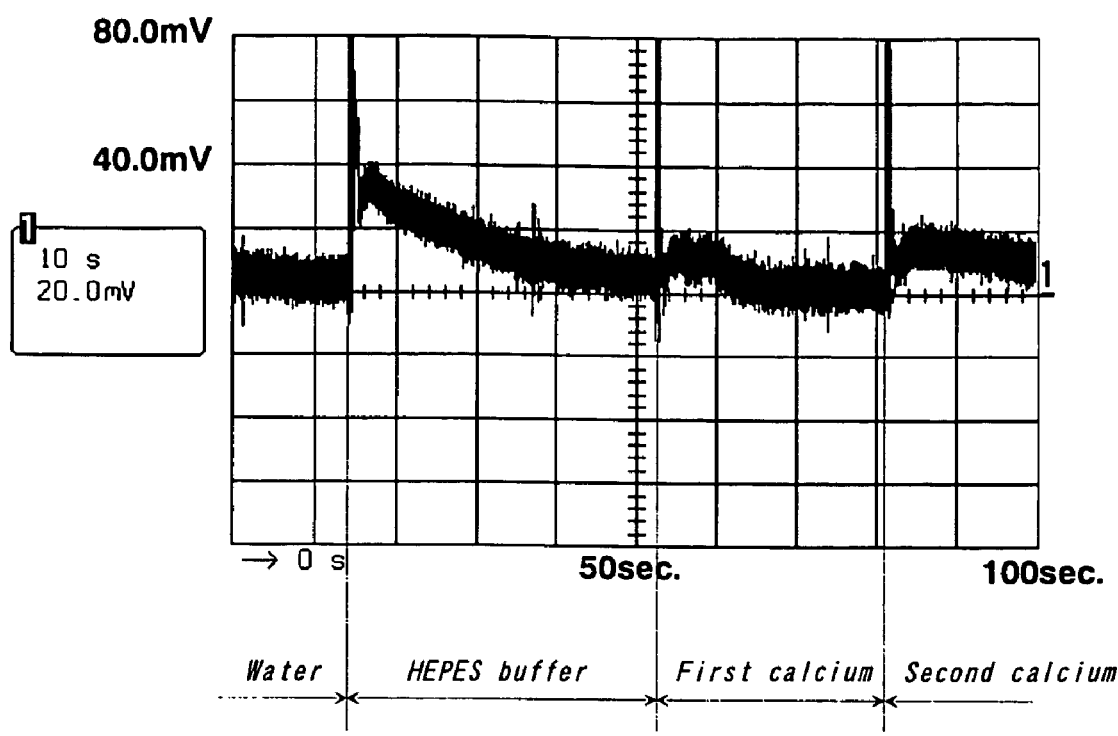
FIG. 7 is a chart representing detection signals produced by a mechanochemical sensor of the invention which is exposed to α-lactablbumin.

FIG. 7 is a chart representing detection signals produced by a mechanochemical sensor of the invention which is exposed to α-lactablbumin.

An epoxy-resin photoresist (MicroChem SU-8) was used to produce a cantilever-based minute structure body, and a metal membrane is formed by vapor deposition on a surface of the structure body to make the structure body electro-conductive. Then, a protein membrane (α-lactalbumin) is formed by ESD over the metal membrane. The deflection of the under-surface of cantilever was monitored by optical lever method, while pure water, buffer solution (HEPES), and calcium solution were sequentially dispensed dropwise. Thus, detection signals were obtained.

Figure 8:
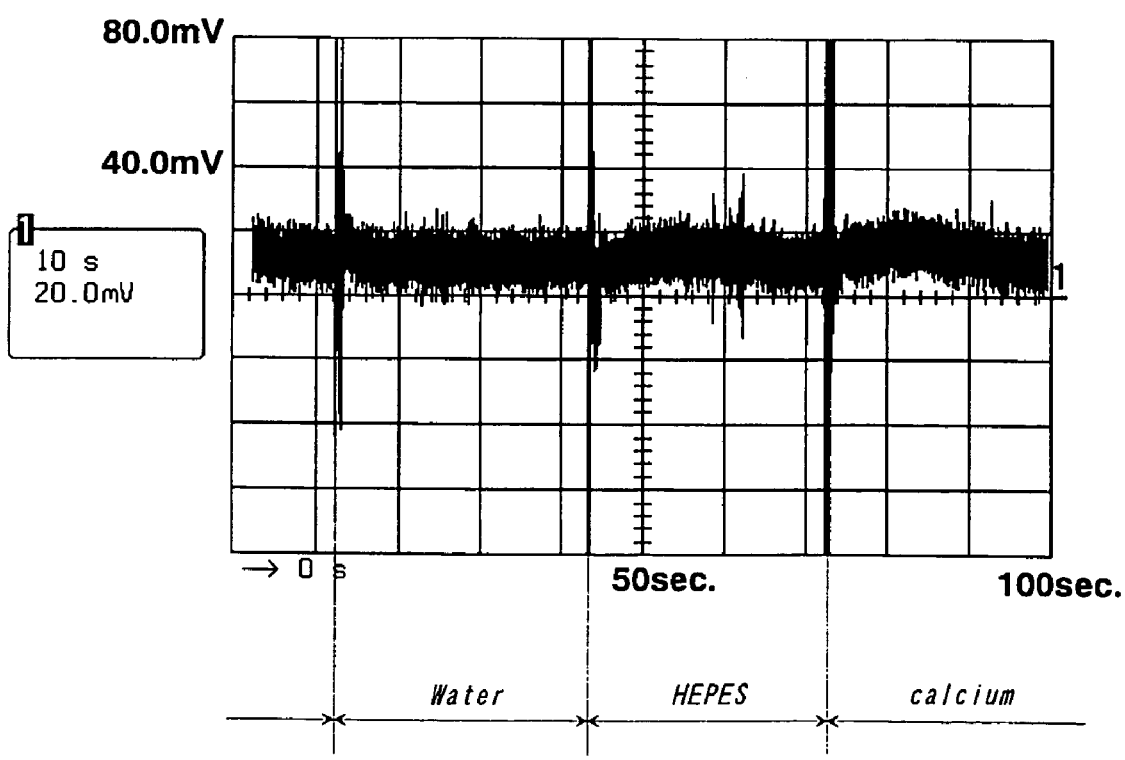
FIG. 8 is a chart obtained from the same experiment in which, however, no protein membrane is formed on the sensor.

A blank test was performed. FIG. 8 is a chart obtained from the same experiment in which, however, no protein membrane is formed on the minute structure body.

As shown in FIG. 7, the detector incorporating a protein membrane exhibited signals indicating the occurrence of some chemical binding (i.e., chemical interaction) between the protein and the calcium ions, while the detector lacking a functional membrane did not exhibit any noticeable signals as seen from the blank test shown in FIG. 8. This demonstrates that the sensor of the invention can detect the presence of minute amounts of substance.

By exploiting specific chemical reactions between functional membranes and substances in liquid, gas, etc., it is possible to use the sensor device of the invention for detecting, quantifying or analyzing minute amounts of substances in liquid or gas, or further for detecting, quantifying or analyzing the change of environment such as surrounding light, temperature, or radioactive rays. The main field to which the present invention can be applied includes, for example, pharmaceutics, biochemical analysis for medicine, analysis of minor organic substances in biochemistry and molecular biology, analysis of proteins and others, chemistry, management of biological plants, water quality control in agriculture, and control of the concentration of material products. Furthermore, the present invention can be used for detecting minor gas in the air, and for measuring light, temperature or radioactivity in the environment.

INDUSTRIAL APPLICABILITY

The principle underlying the present invention has been described in the Specification with reference to various embodiments. However, it should be understood that the present invention is not limited in any way to the embodiments described above, and that those having ordinary skill in the related art will be able to easily develop many variations and modifications based on the disclosure cited in the Specification without departing the spirit and scope of the present invention.

For example, in the embodiments cited above, the sensor is allowed to contact with a target substance in solution. However, the medium with which the sensor contacts is not limited to liquid, but may include any type of medium such as gas, radioactive ray, electromagnetic wave, light, etc., as long as a target substance in the medium can interact with a functional membrane incorporated in the sensor, and thus can be detected or quantified by the sensor.

In the embodiments cited above, the functional membrane is made of protein. More specifically, the membrane may be made of an amorphous protein or a crystalline protein. Alternatively, the membrane may be made of an organic polymer, metal, inorganic ceramic, etc. The sensor does not necessarily take the shape of membrane, but may take a rod-like, fiber-like, or plate-like shape as well as a membrane-like shape.

The mechanical property to be measured may be any appropriate one chosen, for example, from elastic coefficient (longitudinal elasticity, transverse elasticity, Poisson ratio, etc.), internal damping constant, change of the natural length (extension/contraction), etc.

The invention claimed is:

1. A mechanochemical sensor comprising:
a minute mechanical structure body having a supporting portion and a pair of arms connected via elastic hinges to the support portion;
a functional membrane that is connected to both arms;
a detection means for detecting the change of a mechanical property of the functional membrane, the detection means including a force detection sensor that is connected to one of the arms; and
an actuator for providing tension to the functional membrane, the actuator being connected to the other of the arms.

2. A mechanochemical sensor as described in claim 1 wherein:
the minute mechanical structure body comprises a first region having the functional membrane formed on its surface and the first region is a thin layer.

3. A mechanochemical sensor as described in claim 1 wherein the minute mechanical structure body is a plurality of minute structure bodies each comprising a different functional membrane.

4. A mechanochemical sensor as described in claim 1 wherein the functional membrane is made of a biopolymer or a synthetic polymer.

5. A mechanochemical sensor as described in claim 1 wherein the functional membrane is formed directly on a surface of the minute mechanical structure body by electrospray deposition.

6. A mechanochemical sensor as described in claim 5 wherein:
the minute mechanical structure body comprises a zone which will not be displaced or displaced negligibly even when a mechanical property of the functional membrane is changed, and
the minute mechanical structure body has its one end immersed into a test solution such that said zone is close to the surface of the test solution.

7. A mechanochemical sensor as described in claim 6 wherein:
the detection means comprises a force-detection sensor and an actuator for providing a tension to the functional membrane.

8. A mechanochemical sensor as described in claim 6 wherein:
the minute mechanical structure body comprises a minute cantilever having a functional membrane formed thereon; and
the detection means is a sensor capable of detecting the bending deformation of the minute cantilever of minute mechanical structure body.

9. A mechanochemical sensor as described in claim 5 wherein:
   the detection means comprises a force-detection sensor and an actuator for providing a tension to the functional membrane.

10. A mechanochemical sensor as described in claim 9 wherein:
   the minute mechanical structure body comprises a minute cantilever having the functional membrane formed thereon; and
   the detection means is a sensor capable of detecting the bending deformation of the minute cantilever of the minute mechanical structure body.

11. A mechanochemical sensor as described in claim 5 wherein:
   the minute mechanical structure body comprises a minute cantilever having the functional membrane formed thereon; and
   the detection means is a sensor capable of detecting the bending deformation of the minute cantilever of the minute mechanical structure body.

12. A mechanochemical sensor as described in claim 1 wherein the functional membrane is formed directly on a surface of the minute mechanical structure body by ink jet deposition.

13. A mechanochemical sensor as described in claim 12 wherein:
   the detection means comprises a force-detection sensor and an actuator for providing a tension to the functional membrane.

14. A mechanochemical sensor as described in claim 13 wherein:
   the minute mechanical structure body comprises a minute cantilever having the functional membrane formed thereon; and
   the detection means is a sensor capable of detecting the bending deformation of the minute cantilever of the minute mechanical structure body.

15. A mechanochemical sensor as described in claim 14 wherein:
   the minute mechanical structure body comprises a minute cantilever having the functional membrane formed thereon; and
   the detection means is a sensor capable of detecting the bending deformation of the minute cantilever of the minute mechanical structure body.

* * * * *